US010925719B2

(12) United States Patent
Kaplan et al.

(10) Patent No.: US 10,925,719 B2
(45) Date of Patent: Feb. 23, 2021

(54) COVER DEVICE AND METHOD OF APPLYING COVER DEVICE FOR CONSTRUCTING AND PROTECTING A NIPPLE/AREOLA COMPLEX

(71) Applicants: Ivor Barry Kaplan, Norfolk, VA (US); Michael Wade Dahl, Yorktown, VA (US)

(72) Inventors: Ivor Barry Kaplan, Norfolk, VA (US); Michael Wade Dahl, Yorktown, VA (US)

(*) Notice: Subject to any disclaimer, the term of this patent is extended or adjusted under 35 U.S.C. 154(b) by 99 days.

(21) Appl. No.: 15/890,430

(22) Filed: Feb. 7, 2018

(65) Prior Publication Data

US 2018/0221136 A1 Aug. 9, 2018

Related U.S. Application Data

(60) Provisional application No. 62/456,869, filed on Feb. 9, 2017.

(51) Int. Cl.
| A61F 2/12 | (2006.01) |
| A61F 2/52 | (2006.01) |
| A61L 31/04 | (2006.01) |
| A61F 2/10 | (2006.01) |
| A61F 13/14 | (2006.01) |

(52) U.S. Cl.
CPC .............. *A61F 2/12* (2013.01); *A61F 2/105* (2013.01); *A61F 13/14* (2013.01); *A61L 31/048* (2013.01); *A61F 2220/0008* (2013.01); *A61F 2220/0075* (2013.01); *A61L 2430/04* (2013.01)

(58) Field of Classification Search
CPC .............. A61F 2/12; A61F 2/105; A61F 2/52
See application file for complete search history.

(56) References Cited

U.S. PATENT DOCUMENTS

| 4,790,309 | A | | 12/1988 | Becker | |
| 4,870,977 | A | | 10/1989 | Imonti | |
| 5,171,321 | A | * | 12/1992 | Davis | A61F 2/52 128/890 |
| 5,522,892 | A | * | 6/1996 | Lin | A41C 3/144 450/39 |
| 5,683,286 | A | * | 11/1997 | Kielland | A61F 13/141 2/267 |
| 6,537,318 | B1 | * | 3/2003 | Ita | A61F 2/12 623/11.11 |
| 7,487,779 | B2 | | 2/2009 | Kurz et al. | |
| 7,566,344 | B2 | * | 7/2009 | Hansen | A61F 2/52 450/81 |

(Continued)

FOREIGN PATENT DOCUMENTS

WO WO-2015051388 A1 4/2015

*Primary Examiner* — Seema Mathew
(74) *Attorney, Agent, or Firm* — Clayton, McKay & Bailey, PC

(57) ABSTRACT

A cover device may include a body with an inner surface and an outer surface, each of the inner surface and the outer surface extending from a first end face of the body to a second end face of the body. The inner surface may define a channel extending through the body from the first end face to the second end face. The outer surface may define a plurality of grooves extending from the first end face to the second end face. Each of the body, the inner surface, and the outer surface may be configured to elastically deform relative to at least an axis of the channel.

13 Claims, 13 Drawing Sheets

(56) References Cited

U.S. PATENT DOCUMENTS

| | | | |
|---|---|---|---|
| 7,921,851 B2 | 4/2011 | Kurz et al. | |
| 7,938,122 B2 | 5/2011 | Clark | |
| 8,191,554 B2 | 6/2012 | Kurz et al. | |
| 8,628,507 B1 * | 1/2014 | Carroll | A61F 13/141 |
| | | | 604/346 |
| 8,686,214 B2 | 4/2014 | Hyde-Edwards et al. | |
| 8,770,202 B2 * | 7/2014 | Rohrig | A61J 13/00 |
| | | | 128/890 |
| 8,808,262 B2 | 8/2014 | Krasikoff et al. | |
| 8,844,539 B2 * | 9/2014 | Kurz | A61F 13/141 |
| | | | 128/889 |
| 9,254,188 B2 | 2/2016 | Dempsy | |
| 9,687,388 B2 * | 6/2017 | Raniere | A61F 13/14 |
| 10,285,911 B1 * | 5/2019 | Tronson | A61J 11/0005 |
| 10,524,896 B2 * | 1/2020 | Kullas | A61F 2/12 |
| 10,568,785 B2 * | 2/2020 | Moser | A61B 46/23 |
| 10,632,021 B2 * | 4/2020 | Madden | A61F 13/141 |
| 2008/0071370 A1 * | 3/2008 | Vinas | A61F 2/52 |
| | | | 623/7 |
| 2011/0247636 A1 | 10/2011 | Pollack | |
| 2013/0270140 A1 * | 10/2013 | Tronson | B65D 25/00 |
| | | | 206/457 |
| 2014/0060548 A1 * | 3/2014 | Check | A61F 15/008 |
| | | | 128/845 |
| 2014/0305446 A1 * | 10/2014 | Raniere | A61F 13/14 |
| | | | 128/890 |
| 2015/0025628 A1 * | 1/2015 | Langer | A61F 2/52 |
| | | | 623/8 |
| 2016/0262946 A1 * | 9/2016 | Dickson | A61J 13/00 |
| 2017/0065404 A1 * | 3/2017 | Netta Chaim | A61F 2/12 |
| 2019/0336273 A1 * | 11/2019 | Bertoli | A61F 2/12 |
| 2020/0060940 A1 * | 2/2020 | Conneely | A41C 3/04 |

* cited by examiner

COVER DEVICE AND METHOD OF APPLYING COVER DEVICE FOR CONSTRUCTING AND PROTECTING A NIPPLE/AREOLA COMPLEX

This application claims priority to U.S. provisional patent application No. 62/456,869 ("Cover Device and Method of Applying Cover Device for Constructing and Protecting a Nipple/Areola Complex"), filed Feb. 9, 2017, which is incorporated by reference in its entirety.

TECHNICAL FIELD

The present disclosure relates to a device and method for constructing and protecting surgically reconstructed tissue structures. More specifically, the present disclosure relates to a device that can be utilized to construct a protruding tissue structure, such as a nipple of a nipple/areola complex, and protect such protruding tissue structure once securing elements, such as sutures, have been removed.

BACKGROUND

Breast reconstruction may follow breast removal (mastectomy) of a breast that is diseased or has suffered irreparable trauma. There are a number of different methods used for breast reconstruction, one of which may involve the insertion of a permanent breast implant either directly at the time of breast removal, or at a later date when a temporary spacer device (tissue expander) placed under retained breast skin is removed. Other reconstruction methods may involve a transfer of tissue from other sites on a body of a patient to the breast to recreate a breast mound. In a majority of breast removals, a nipple and areola complex (hereafter referred to as "NAC") is removed with breast tissue, but a large portion or all of the skin of the breast is retained (so called "skin sparing mastectomy"). Accordingly, a majority of breast reconstruction procedures involve nipple and areola reconstruction (NAC reconstruction), regardless of the breast reconstruction method employed.

NAC reconstruction follows an initial creation (reconstruction) of the breast mound and can be achieved in a number of different ways. A realistic NAC reconstruction aids in achieving a realistic looking breast, and may provide tangible psychological benefits to a patient undergoing breast reconstruction. Accordingly, nipple size, projection, position, shape, and color are key considerations in the NAC reconstruction process. Although NAC reconstruction may be done by artful tattooing alone, the most realistic NAC reconstructions often involve: (1) a surgical production of a small skin/fat protuberance (a reconstructed nipple); and (2) a production of a circular flat surface (a reconstructed areola) surrounding the reconstructed nipple that is usually of a different color and/or texture from surrounding breast skin (as is normally present in the intact breast).

The reconstructed nipple may be formed from small flaps of skin (e.g. a skate flap, S flap, C-V flap, star flap, etc.) (e.g. skate flaps or S flaps) elevated from a surface of the breast and rearranged and sewn together in such a way as to produce a projecting neo nipple. The reconstructed areola may be created by subsequent tattooing of the surrounding breast skin or formally created by a surgical application of a skin graft placed around the fabricated central projecting nipple construct (reconstructed nipple).

For NAC reconstruction procedures utilizing skin grafts to reconstruct the areola, it is important to apply pressure to the skin graft in order to facilitate revascularization by, and more importantly attachment with, an underlying bed of tissue. Subsequent to (7 to 10 days) the NAC reconstruction procedure involving the combined nipple and areola reconstructions, pressure must be continuously and evenly applied to the surface of the skin graft to prevent gaps between the bed and the skin graft from developing that may put the skin graft at risk of dying and having to be replaced.

Whether or not a skin graft is employed in the areola reconstruction, the reconstructed nipple is generally formed as mentioned above, from a flap of skin that is part of spared skin of the (mastectomized) breast. Alternatively, the reconstructed nipple may be formed from a part of skin of a flap that has been brought up to a chest of the patient to make the breast mound if implants alone are not utilized for the breast reconstruction. The reconstructed nipple may however, have a tendency to "slump" or become less protruding from the breast if it is not somehow maintained in an upright position relative to the breast. The reconstructed nipple, immediately after a respective reconstruction, is vulnerable and must be protected similar to a skin graft used for an areola reconstruction. For example, tensile/pulling forces from scar tissue formation or putting on articles of clothing, such as garments and breast support devices (e.g. bra), or slipping bandages, may pull apart sutures used to construct and hold the nipple together and cause the nipple to structurally fail. Further, the articles of clothing mentioned above can place pressure on and compress the reconstructed nipple, resulting in a flattening thereof and prevention of the reconstructed nipple from obtaining a desired appearance.

Surgeons often fabricate what is known as a "bolster" from cotton soaked in mineral oil and saline, and secure the bolster over the NAC. Using this technique, a reconstructed nipple will be surrounded by cotton wool pledgets soaked in saline and mineral oil and layered to be built up to, or slightly higher than, a height of the reconstructed nipple. Further, the bolster may be secured to the NAC with the intention to apply pressure to the skin graft and protect the reconstructed nipple (the flap of the nipple) from direct pressure during a healing process.

As may be easily understood by one of ordinary skill in the art, a bolster must be arranged very carefully around a nipple reconstructed from a skin flap at a center of an areola reconstructed from a skin graft so as not to compress and damage the reconstructed nipple. In addition, such a handmade bolster device cannot continue to be utilized to protect the NAC in the weeks following surgery. Therefore, many surgeons resort to subsequent improvised handmade devices, for example, by cutting holes in gauze and stacking the gauze one on the other to build up a protective cylinder around the reconstructed nipple. The perforated gauze pads may be stacked to the same height or slightly above the nipple height and then medical tape or clear sticky adhesive plastic sheeting may be applied over the gauze pads and on to the surrounding breast to prevent shifting.

Other methods attempted to protect a reconstructed nipple have included cutting a top end off a plastic syringe barrel with a blade or hot cautery device to a height slightly more than the height of the reconstructed nipple. The barrel of the syringe segment may be placed over the reconstructed nipple with a small flanged edge at a top of the cut off barrel placed on the breast skin around the reconstructed nipple. The cut off barrel may be secured with medical tape or some type of suture arrangement to prevent this cumbersome arrangement from dislodging and crushing the reconstructed nipple. However, like other processes of creating objects by hand, it can be difficult to expediently cut a syringe time after time and obtain uniform results. As a result, there is no guarantee that a first device formed from a syringe barrel will be suitable for use. Thus, in addition to a lack of repeatable options yielding uniformly configured devices that apply pressure to skin grafts, there is also lack of options for easily and reliably protecting a reconstructed nipple after surgery.

The varied techniques mentioned above involve time-consuming and often messy procedures that must be performed on the fly in an operating room (OR).

A dressing such as or similar to the bolster described above, may remain on a patient for several days after the nipple or NAC reconstruction surgery. During a patient follow-up meeting, the reconstructed nipple or NAC may be redressed in a similar fashion for continued protection as was provided in the OR. For a period of several weeks after the surgery, the patient may be instructed to reapply a protective dressing after showering, not to wear a compressive bra, and not to undertake any activities where the sutures and integrity of the reconstructed nipple could be compromised. Thus, the patient may be required to take numerous precautions involving time consuming and difficult redressing of the reconstructed nipple for an appreciable time after surgery.

These and other issues are solved by a cover device and method of applying a cover device for constructing and protecting a nipple/areola complex, of the present disclosure.

SUMMARY

According to an aspect of the present disclosure, a cover device may include a body with an inner surface and an outer surface, each of the inner surface and the outer surface extending from a first end face of the body to a second end face of the body. The inner surface may define a channel extending through the body from the first end face to the second end face. The outer surface may define a plurality of grooves extending from the first end face to the second end face. According to an aspect of the present disclosure, each of the body, the inner surface, and the outer surface may be configured to elastically deform relative to at least an axis of the channel.

According to an aspect of the present disclosure, a method of constructing and protecting nipple areola complex of a breast includes suturing a skin graft corresponding to an areola of the nipple/areola complex in a de-epithelialized bed surrounding a nipple of the nipple/areola complex. The method may include leaving a plurality of long sutures during the suturing, each of the plurality of long sutures extending over a length from an outer circumference of the skin graft that is equal to at least twice the diameter of the skin graft. According to an aspect of the present disclosure, the method may include positioning a cover device relative to the nipple/areola complex such that the nipple is positioned within a channel defined by an inner surface of the cover device with a cap of the nipple positioned between a first end face and a second end face of the cover device, and the second end face abuts a surface of the skin graft. According to another aspect of the present disclosure, the method further may include positioning each of the plurality of long sutures in a respective groove defined by an outer surface of the cover device, and tying the plurality of long sutures together at the first end face such that the cover is secured to the nipple/areola complex with the second end face in fixed abutment with the surface of the skin graft.

According to another aspect of the present disclosure, a breast support device includes a first cup and a second cup. At least on of the first cup and the second cup may include a padded region extending from a surrounding edge to an intermediate edge, and a continuous elastic region extending from the intermediate edge. According to an aspect of the present disclosure, the continuous elastic region may include a seam that is concentric with the intermediate edge and a plurality of strips provided on an inner cup surface extending from the seam toward a center of the continuous elastic region.

According to a still further aspect of the present disclosure, a cover device includes a body including an inner surface and an outer surface, each of the inner surface and the outer surface extending from a first end face of the body to a second end face of the body. An outer diameter of the first end face may be less than a outer diameter of the second end face, the inner surface may define a channel extending through the body from the first end face to the second end face, and the outer surface may define a plurality of grooves extending from the first end face to the second end face. According to an aspect of the present disclosure, the body may be formed of ethyl vinyl acetate.

BRIEF DESCRIPTION OF THE DRAWINGS

The disclosure will be best understood through consideration of, and with reference to, the following figures, viewed in conjunction with the Detailed Description, and in which.

The figures presented are intended solely for the purpose of illustration and they are, therefore, neither desired nor intended to limit the subject matter of the disclosure to any or all of the exact details of construction shown, except insofar as they may be deemed essential to the claims.

DETAILED DESCRIPTION

Aspects of the disclosure will now be described in detail with reference to the figures, wherein like reference numbers refer to like elements throughout, unless specified otherwise. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Aspects of the present disclosure described herein are directed toward a cover device for reconstructing and protecting a nipple alone or a nipple/areola complex (NAC). The cover device may include a dome shaped body including an inner surface that defines a channel, and an outer surface that defines a plurality of grooves configured to receive sutures. A head of the body may define a first end face that is flat and defines a plurality of notches; each notch may extend from a first groove end of a respective groove. Further, a base of the body may define a second end face that is flat and defines second groove ends for each groove. In addition, the body may be elastically deformable.

The cover device may be positioned on a reconstructed NAC during a nipple reconstruction procedure. The cover device may be secured to the NAC by sutures that are received in respective grooves and tied together at the first end face over the channel, which surrounds a nipple of the NAC. In this configuration, the cover device is deformed by the compressive force of the tied sutures, but maintains a shape of the second end face to transmit the force and evenly apply pressure to the skin graft. The continuous and evenly applied pressure thereby reliably facilitates vascularization and attachment of the skin graft with a de-epithelialized bed formed on a breast. Concurrently, the channel holds the nipple of the NAC in an upright position protruding from the breast and protects the nipple. Once the sutures are removed, the same or new cover device may be positioned on the NAC between a breast support device and the breast and used to protect the NAC (in particular the nipple of the NAC) from being compressed or rubbed by garments worn by a patient.

Figure 1:
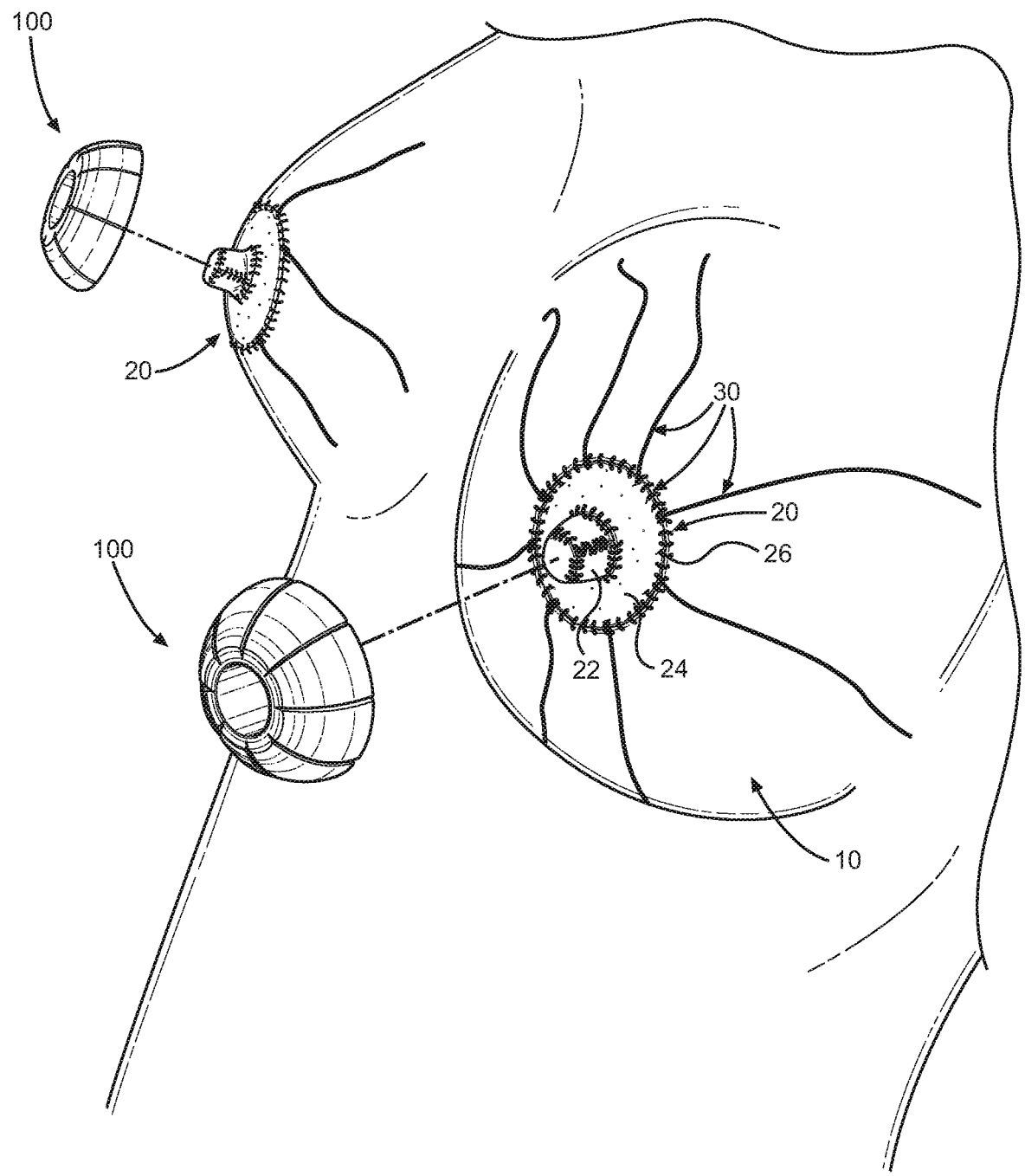
FIG. 1 illustrates a perspective view of a breast and a cover device, according to an aspect of the present disclosure.

FIG. 1 illustrates a perspective view of a breast 10 and a cover device 100 following a nipple reconstruction procedure, according to an aspect of the present disclosure. The breast 10 includes a nipple/areola complex 20 (hereafter referred to as "NAC 20" or "reconstructed NAC 20") that has have been reconstructed. The NAC 20 may include a nipple 22, and a skin graft 24. The skin graft 24 corresponds to an areola of the reconstructed NAC 20 and may be attached to a circumferential skin edge 26 with sutures 30.

According to one aspect of the present disclosure, the cover device 100 may have a mushroom top or dome-like shape as illustrated in FIG. 1, and as explained in more detail below with reference to FIGS. 2A-2D. Further, the cover device 100 may be secured onto the NAC 20 by some of the sutures 30 (left long for that purpose), with the nipple 22 inserted into the cover device 100 as explained in more detail with reference to FIGS. 4A-4I.

Figure 2A:
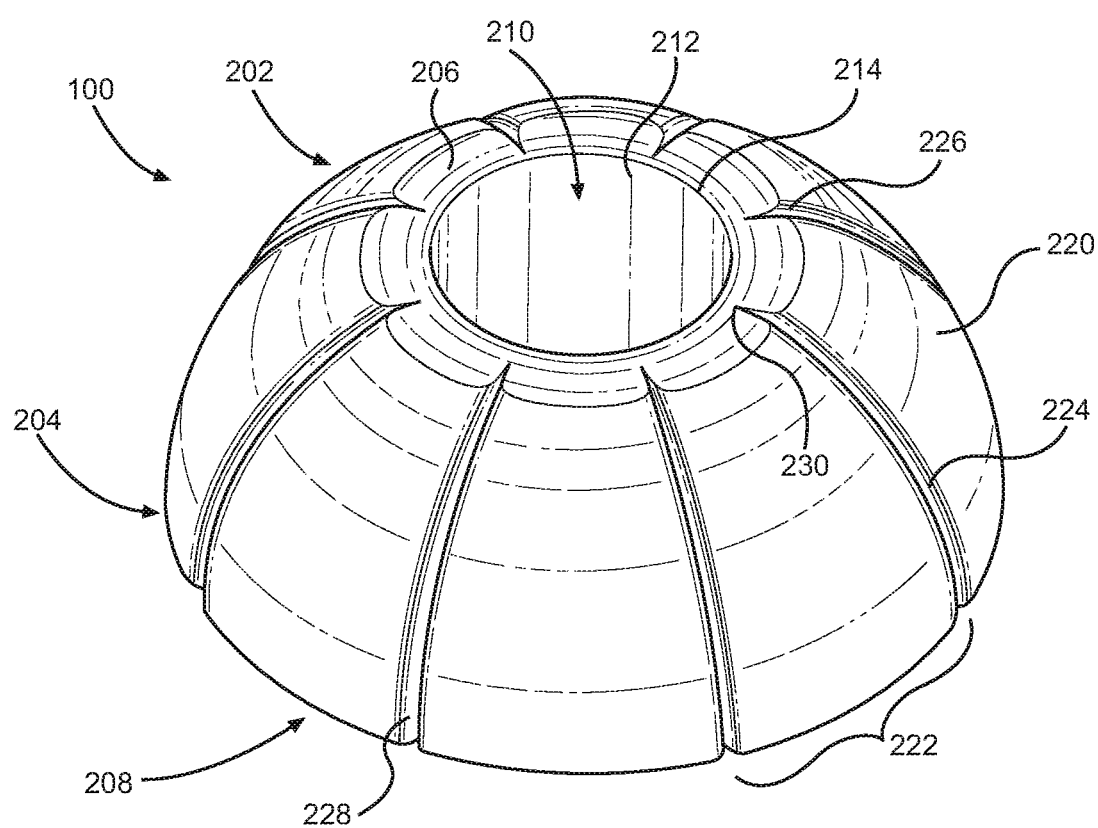
FIG. 2A illustrates a top perspective view of a cover device, according to an aspect of the present disclosure.

FIG. 2A illustrates a top perspective view of the cover device 100, according to an aspect of the present disclosure. The cover device 100 includes a body 200 that is mushroom or dome-like in shape and includes a head 202 and a base 204. The head 202 defines a first end face 206, and the base 204 defines a second end face 208 of the body 200; each of the first end face 206 and the second end face 208 being flat. A channel 210 is defined by an inner surface 212 of the body 200 and extends between respective apertures 214 defined in the first end face 206 (FIGS. 2A, 2C) and the second end face 208 (FIG. 2D). Thus, the channel 210 may be in the form of a cylindrical conduit or tube as illustrated in FIG. 2A.

An outer surface 220 of the body 200 is composed of a plurality of wall segments 222 as provided by grooves 224 defined by/formed in the outer surface 220. Each groove 224 extends from the first end face 206 to the second end face 208. More specifically, each groove 224 extends from a first groove end 226 formed in the first end face 226, to a second groove end 228 formed in the second end face 208. Each first groove end 226 extends from a perimeter of the first end face 206 and terminates in the form of a notch 230 in the first end face 206.

Figure 2B:
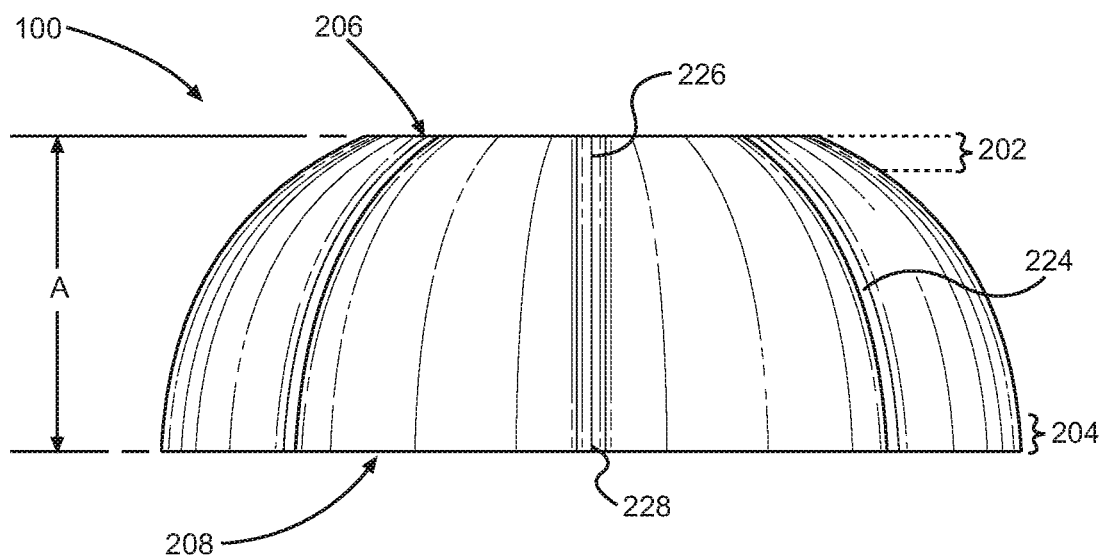
FIG. 2B illustrates a side elevation view of a cover device, according to an aspect of the present disclosure.

FIG. 2B illustrates a side elevation view of the cover device 100, according to an aspect of the present disclosure. As illustrated in FIG. 2B, the body 200 has a height A that may be in a range of 1.3 to 1.7 cm. According to an aspect of the present disclosure, the height A may be 1.5 cm.

FIG. 2B further illustrates a curvature of the wall segments 222 and the grooves 224 as defined by the shape of the outer surface 220. It will be understood that the body 200, and therefore the outer surface 220, may be in the form of other shapes such as a polygon, a pyramid, a square, etc. More generally, the body 200 may be formed into a shape that facilitates the placement of the sutures 30 within the grooves 224, and tying of the sutures 30 at the first end face 206 to secure the cover device 100 to the NAC 20.

Figure 2C:
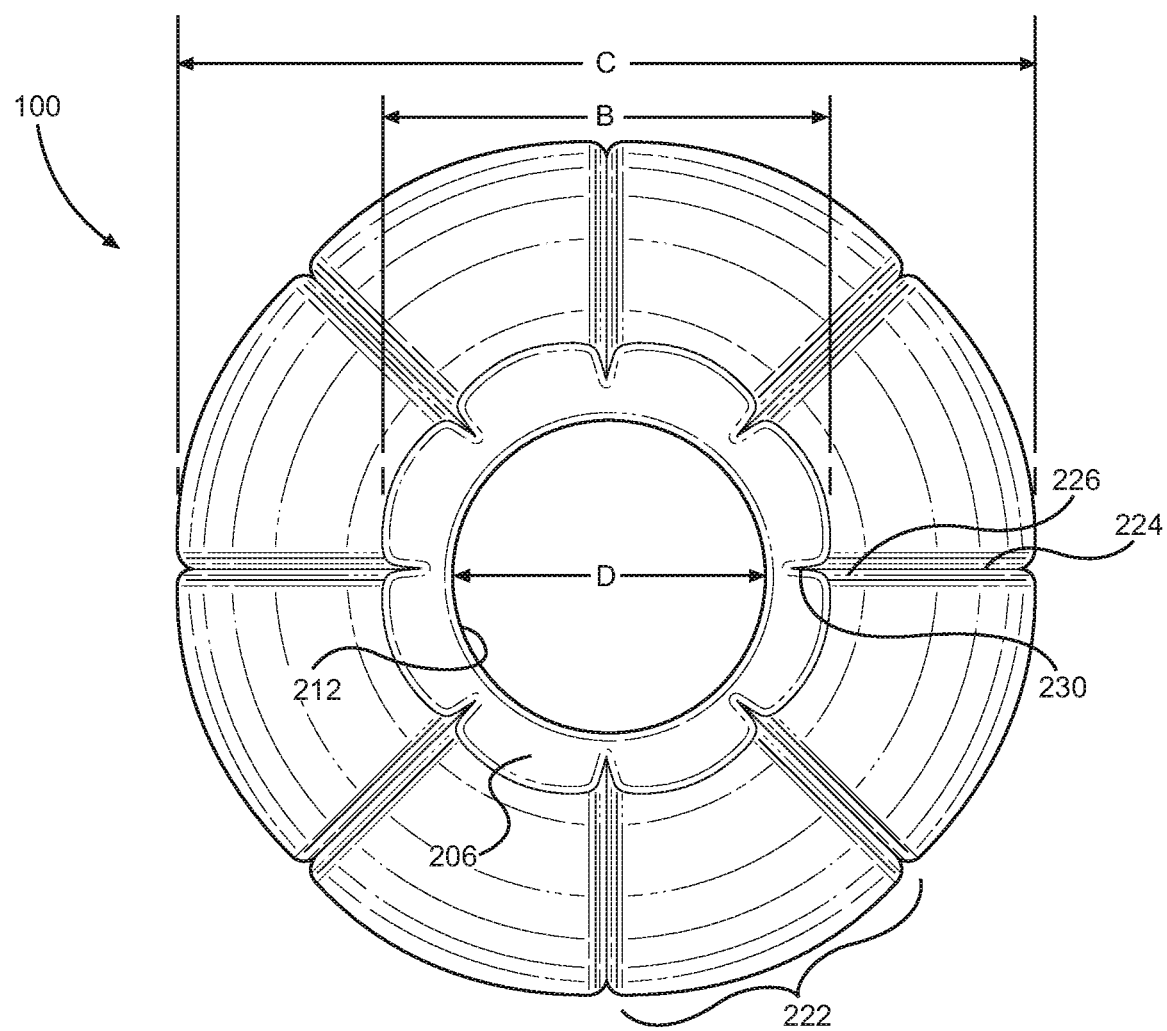
FIG. 2C is a top view of a cover device, according to an aspect of the present disclosure.
Figure 2D:
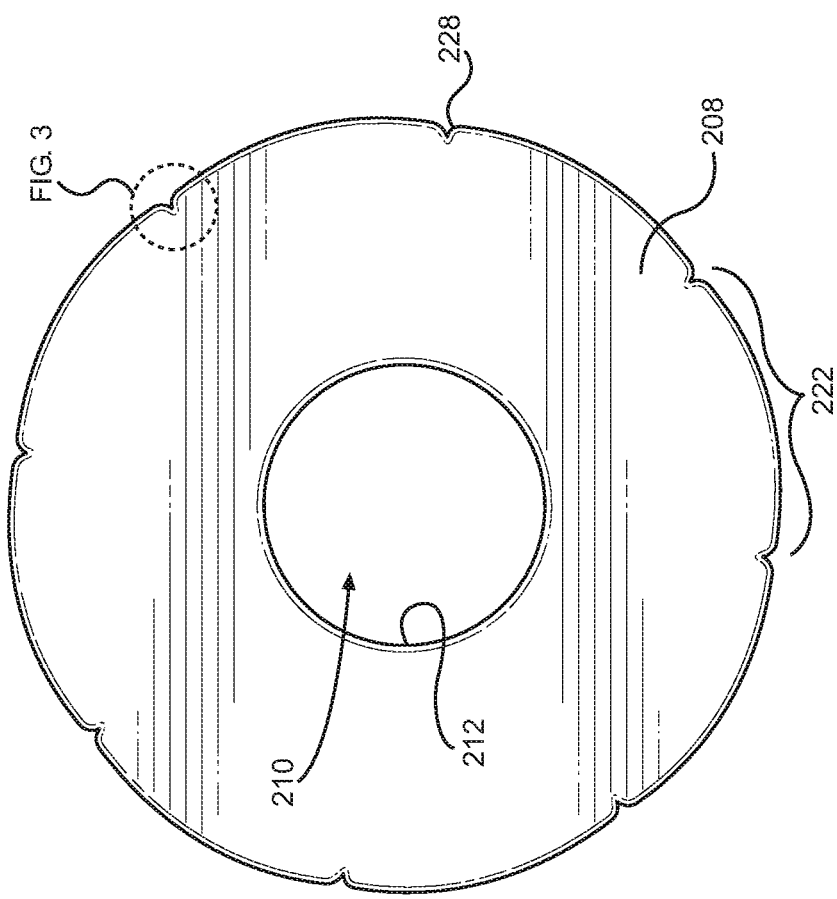
FIG. 2D is a bottom view of a cover device, according to an aspect of the present disclosure.

FIG. 2C is a top view of the cover device 100, according to an aspect of the present disclosure. As illustrated in FIG. 2C, the cover device 100 has a first outer diameter B corresponding to a diameter of the perimeter of the first end face 206, and a second outer diameter C as defined by a diameter of a perimeter of the base 204. The first outer diameter B may be in a range of 1.7 to 2.2 cm, and the second outer diameter C may be in a range of 4.3 to 4.7 cm. According to an aspect of the present disclosure, the first outer diameter B may be 1.9 cm and the second outer diameter C may be 4.5 cm. In addition, the channel 210 may have a channel diameter D in a range of 1.4 to 1.6 cm, and may preferably be 1.5 cm. The ranges for the dimensions discussed herein are exemplary. One of ordinary skill in the art will recognize that dimensions of the cover device 100 may be adjusted to match a size of the NAC 20 desired by a surgeon and/or patient and vice versa. According to another aspect of the present disclosure, the cover device 100 may be provided in a range of standardized sizes since a surgeon may be able to construct the NAC 20 to be a desired size corresponding to a size of the cover device 100.

FIG. 2C further illustrates notches 230, each of which extends from a respective first groove end 226 defined by the body 200. According to an aspect of the present disclosure, the curved slope of each groove 224 and first groove end 226, combined with a respective notch 230 defines a continuous transition (e.g. a ramp) from the first groove end 226 to a flat surface of the first end face 206. Accordingly, the first groove end 226 and the notch 230 may guide an element, such as a suture 30, from a respective groove 224 onto the flat surface of first end face 206 without causing the suture 30 to bend or "kink" at a sharp angle (e.g. 90°) as the suture 30 transitions from the groove 224 to the surface of the first end face 206. As a result, when the suture 30 is tied to the other sutures 30, an angle of a direction along which a downward force (i.e. vector) is applied to the first end face 206 by each suture 30 is closer to a direction that is normal to a surface of the skin graft 24. In contrast, a configuration in which a suture 30 bends around a corner at the outer perimeter of the first end face 206 at a sharp angle as described above, may apply a force along a direction that is closer to a direction parallel to the surface of the skin graft 224.

One of ordinary skill in the art will understand that an amount of pressure applied to the skin graft 24 by the second end face 208 is proportional to a magnitude of a downward force normal to a surface of the skin graft 24. According to one aspect of the non-limiting exemplary configuration of the cover device 100 illustrated in FIGS. 1-2D, forces applied by sutures 30 may be directed more towards the second end face 208 (and therefore closer to a direction normal to the surface of the skin graft 24) than the inner surface 212 as a result of the continuous transition provided by the combination of the curvature of the groove 224, the first groove end 226, and the notch 230. This may cause the second end face 208 to be more directly pressed against the surface of the skin graft 24 (i.e. apply more pressure to the skin graft 24) than if the suture 30 was caused to bend around a corner between the first end face 206 and the outer surface 220 at a sharp angle as previously discussed.

However, it will be understood that an optimal amount of pressure that may be applied to a given skin graft of a reconstructed NAC may vary depending on the type of skin graft (e.g. split-thickness, full-thickness) being used. According to one aspect of the present disclosure, a transition between at least the first groove ends 224 (as well as the outer surface 220) and the first end face 206 may be configured according to the optimal pressure to be applied to the surface of the skin graft 24, as dictated by the type of skin graft employed to construct the NAC 20. Accordingly, the present disclosure is not limited to the particular transitions (e.g. ramp) provided by the first groove ends 224 and notches 230 illustrated in FIGS. 1-2D.

FIG. 2D is a bottom view of the cover device 100, according to an aspect of the present disclosure. As illustrated in FIGS. 2B and 2D, the second end face 208 defines a flat annular surface that surrounds the aperture 214 of the channel 210. The flat annular surface may be configured with the second outer diameter C sized to correspond to a desired circumferential skin edge 26 (FIG. 1) or vice versa. Unlike a bolster described above, the flat annular surface of the second end face 208 may apply pressure evenly over the surface area of the surface of the skin graft 24. As a result, the skin graft 24 may be more uniformly pressed against a de-epithelialized bed and more effectively re-vascularized in comparison to a procedure utilizing a device or instrument that is not substantially flat or able to uniformly transmit a downward force applied by a device securing mechanism (e.g. tape, sutures, etc.), such as a bolster.

Figure 3:
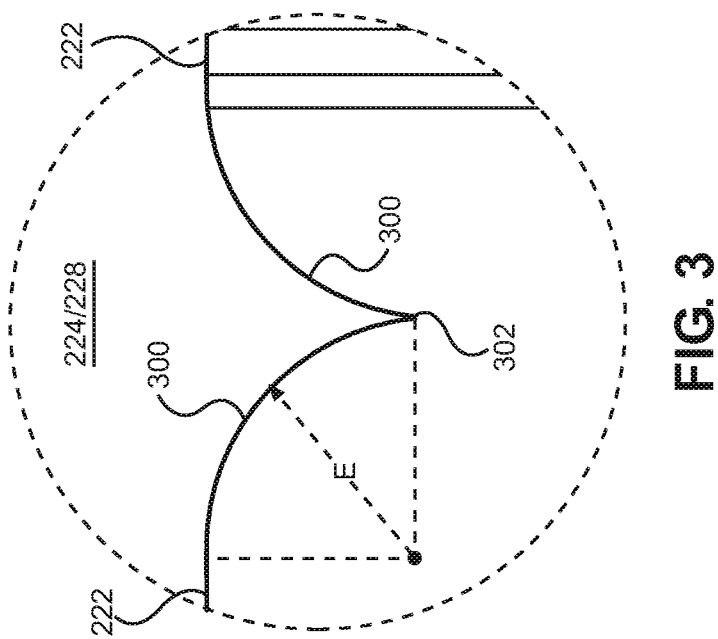
FIG. 3 is an enlarged view of a portion of FIG. 2D designated as Detail 3 and includes a view of one groove of a cover device.

As further illustrated in FIG. 2D, the second groove ends 228 open on to the flat annular surface of the bottom end face 208. FIG. 3 is an enlarged view of a portion of FIG. 2D designated as Detail 3 and includes a view of one second groove end 228 of the cover device 100. According to an aspect of the present disclosure, the second groove end 228 and a majority of the groove 224 including a portion of the first groove end 226, are defined by groove walls 300 formed/defined by the outer surface 220 of the body 200 as illustrated in FIG. 3. It will be noted that at the first groove end 226, the groove walls 300 transition from the profile illustrated in FIG. 3 into the notches 230 at the first end face 206. According to an aspect of the present disclosure, the groove walls 300 are curved surfaces such that a cross-section of the groove 224 has a curved V-shape. According to another aspect of the present disclosure each groove wall 300 may have a radius curvature E in a range of 0.8 to 1.2 mm, and may preferably be 1.0 mm.

As illustrated in FIG. 3, the groove walls 300 extend from a joint edge 302 to an outermost portion of the outer surface 220, which defines the wall segments 222. The groove walls 300 are symmetric about the joint edge 302 that is located at a center of a trench defined by the groove 224. The cross-section of the groove(s) 224 is continued over a length of the groove(s) 224 from the second groove end 228 to the first groove end 226. As a result the wall segments 222 may be lobe-shaped as illustrated in FIGS. 2A, 2C, and 2D. However, it will be understood that other shapes (e.g. a flat angled wall, a wall extending 90° from a horizontal surface, an inwardly curved or parabolic surface, etc.) may be employed for the groove walls 300 such that the grooves 224 have different cross-sectional shapes (e.g. a straight V-shape, a square, a semi-circle, etc.). More generally, the groove walls 300 may have any shape, including a shape that define the grooves 224 to have asymmetrical cross-sections, that enables the grooves 224 to prevent the sutures 30 from moving radially relative to respective grooves 224.

According to an aspect of the present disclosure, the body 200 of the cover device 100 may be formed of a material that is elastically deformable. More specifically, the body 200 may be formed from an elastically deformable sponge-like material that is compressible. For example the cover device 100 may be formed from certain types of thermoplastic materials such as ethyl vinyl acetate or other foam rubber materials. Further, the cover device 100 may be formed from a sheet of elastic material, such as a sheet formed from ethyl vinyl acetate. More specifically, the cover device 100 may be cut from the sheet alone, or cut from the sheet of elastic material and further molded into shape.

Figure 4A:
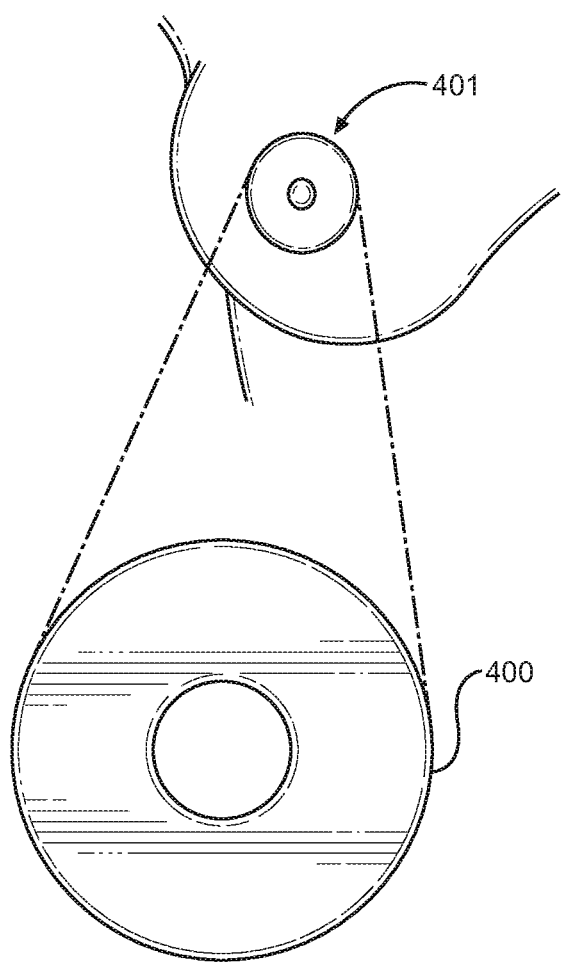
FIG. 4A illustrates a process of designating a proposed position of a nipple/areola complex (NAC) for a method of constructing and protecting a NAC, according to an aspect of the present disclosure.

FIGS. 4A-4I illustrate a method of constructing and protecting a NAC 400 (hereafter referred to as "NAC constructing method 400"), according to an aspect of the present disclosure. In particular, FIG. 4A illustrates a process of designating a proposed NAC position 401 that includes drawing two concentric circles on a breast, such as the breast 10 illustrated in FIG. 1 prior to reconstruction of the NAC 20. The outer circle corresponds to an outer diameter of an areola to be provided by a skin graft, such as the skin graft 24 illustrated in FIG. 1. The inner circle corresponds to a location of a base of a nipple to be constructed, such as the nipple 22 illustrated in FIG. 1.

Figure 4B:
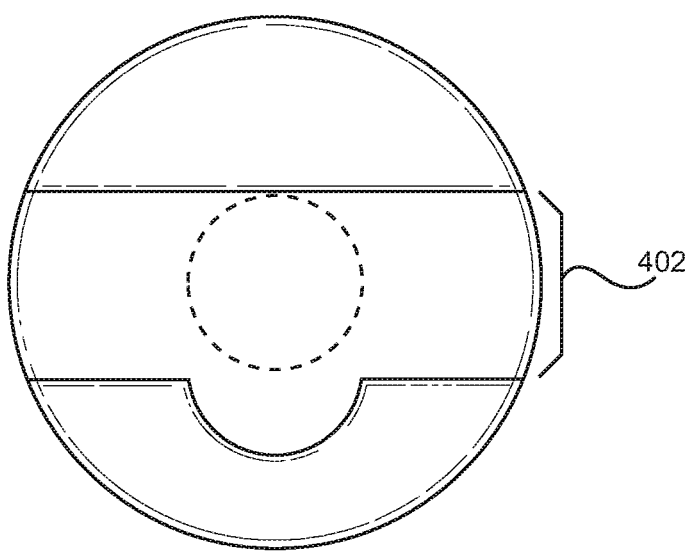
FIG. 4B illustrates a process of designating a position of a flap, according to an aspect of the present disclosure.

FIG. 4B illustrates a process of designating a flap outline 402, according to an aspect of the present disclosure. The flap outline 402 may be drawn on the breast to designate a line(s) for making an incision(s) to construct a nipple from a resulting flap (e.g. a skate flap, S flap, C-V flap, star flap, etc.). In general, a nipple may be reconstructed from an incised local flap of skin on the breast mound and fat tissue that are elevated together from a breast mound to create a protrusion. Typically, the incised local flap is closed by suturing opposing skin edges thereof together to form the nipple.

Figure 4C:
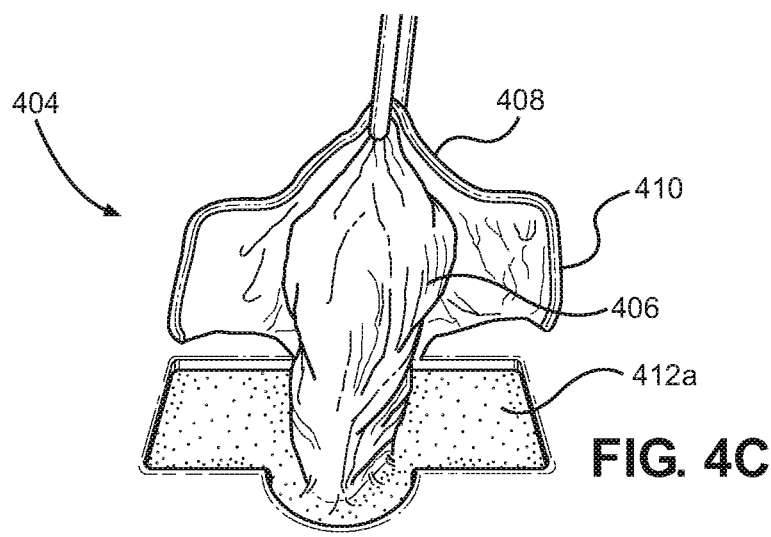
FIG. 4C illustrates a process of elevating a flap on a pedicle core, according to an aspect of the present disclosure.

As illustrated in FIG. 4C, a flap 404 is created with a series of incisions made along the flap outline 402. A portion of the flap 404 will remain attached to an initial de-epithelialized bed 412a, which is created by making the incisions and pulling the flap 404 from the initial de-epithelialized bed 412a. FIG. 4C illustrates such a process of elevating a flap 404 on a pedicle core 406 for the NAC constructing method 400, according to an aspect of the present disclosure. The pedicle core 406 will remain connected to the initial de-epithelialized bed 412a and continue to provide a blood supply and vascularize the flap 404 once it is formed, thereby keeping the flap 404 alive. As illustrated in FIG. 4C, the exemplary flap 404 includes a cap 408 attached to the pedicle core 406 and wings 410 on opposite sides of the pedicle core 406.

Figure 4D:
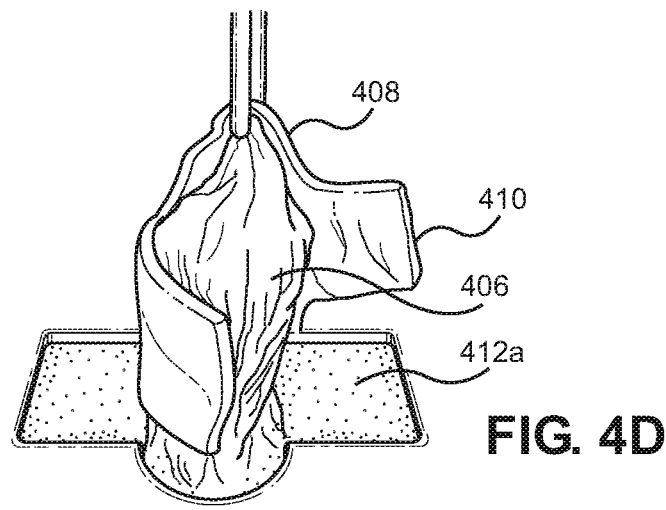
FIG. 4D illustrates a process of wrapping a flap around a pedicle core, according to an aspect of the present disclosure.

FIG. 4D illustrates a process of wrapping the flap 404 around the pedicle core 406, according to an aspect of the present disclosure. In particular, the wings 410 are wrapped around the pedicle core 406 and the cap 408 is folded over the pedicle core 406 to form a cylindrical body and the tip of the nipple 22. Subsequent to wrapping the flap 404, the wings 410 are sutured to each other and the cap 408 is sutured to top edges of the wings 410 to thereby form a protruding tissue structure of the nipple 22 as shown in FIG. 4E.

Figure 4E:
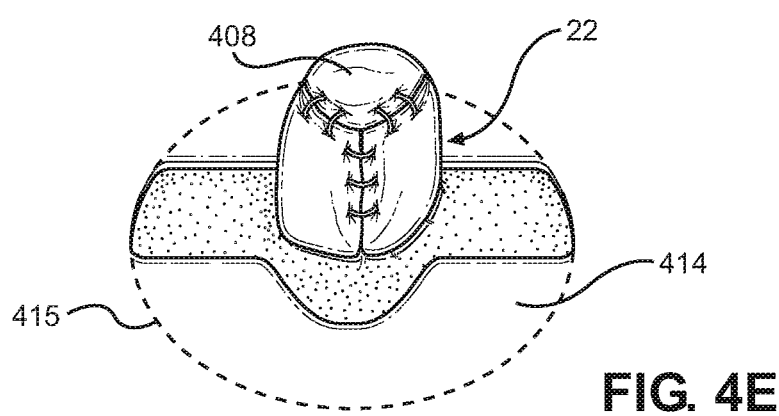
FIG. 4E illustrates a process of designating additional skin for removal from a breast, according to an aspect of the present disclosure.

FIG. 4E illustrates a process of designating additional skin 414 for removal from the breast 10, according to an aspect of the present disclosure. The circular dotted outline 415 illustrated in FIG. 4E is used to designate the location of one or more incisions to be made in order to remove the additional skin 414 that is radially between the nipple 22 and the circular dotted outline 415 (except for the portion of the flap attached to the initial de-epithelialized bed 412b). Once the additional skin 414 is removed, a circumferential skin edge, such as the circumferential skin edge 26 illustrated in FIG. 1, is formed and an expanded de-epithelialized bed 412b (hereafter referred to as "bed 412b") is exposed. The size and shape of the bed 412b corresponds to an areola to be formed by a skin graft such as the skin graft 24 illustrated in FIGS. 1 and 4E. One of ordinary skill in the art will recognize that a surgeon can form the circumferential skin edge 26 to have a diameter that corresponds to the second diameter B of a standardized version of the cover device 100.

Figure 4F:
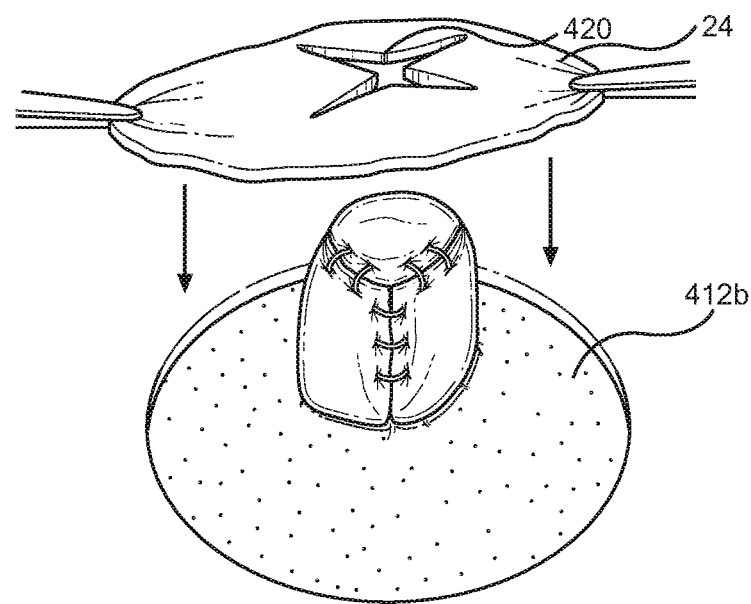
FIG. 4F illustrates a process of positioning a skin graft on to an initial de-epithelialized bed, according to an aspect of the present disclosure.

FIG. 4F illustrates a process of positioning the skin graft 24, according to an aspect of the present disclosure. The skin graft 24 includes an incision cruciate 420, and is fitted into the bed 412b with the protruding tissue structure that is the nipple 22 projecting through the incision cruciate 420.

Figure 4G:
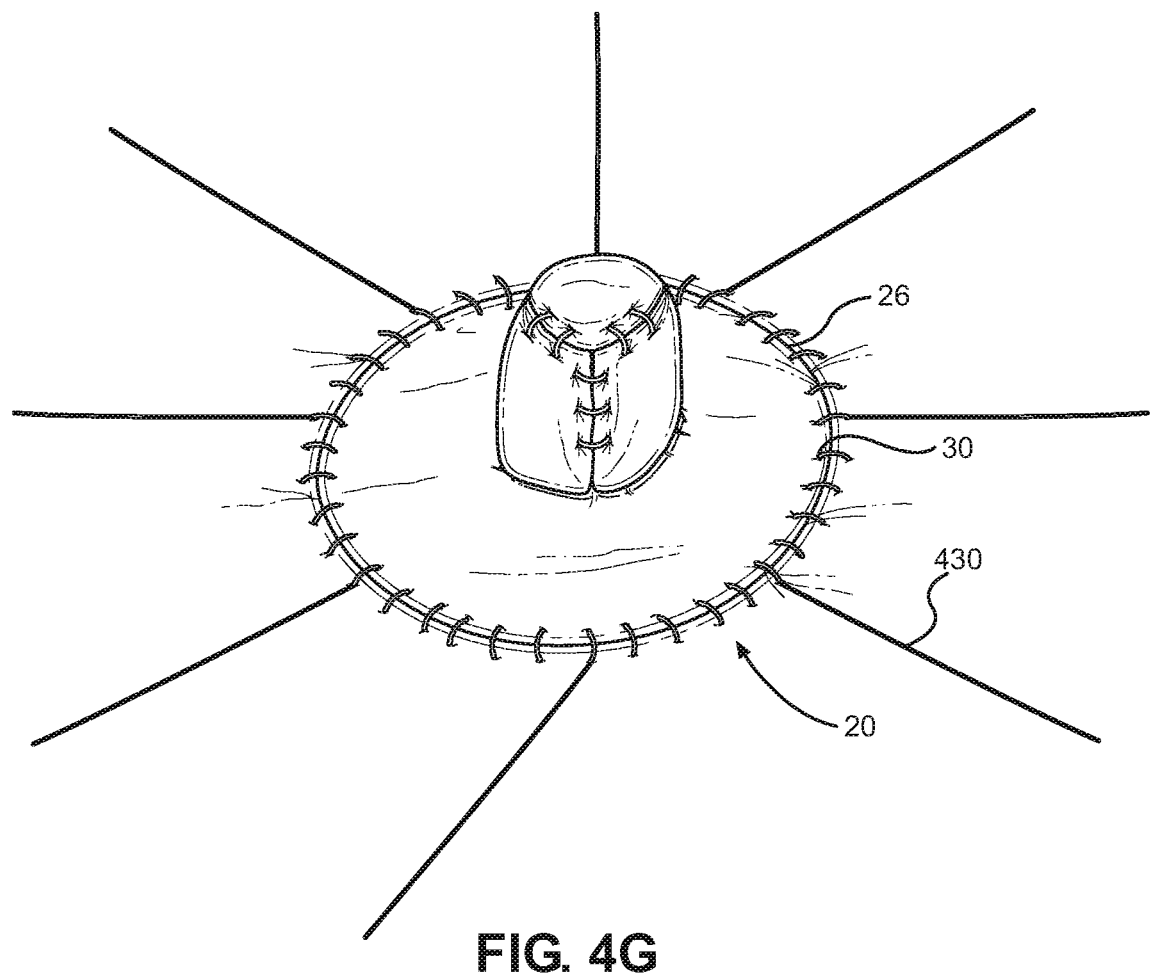
FIG. 4G illustrates a process of suturing a skin graft in an expanded de-epithelialized bed, according to an aspect of the present disclosure.

FIG. 4G illustrates a process of suturing the skin graft 24 in the bed 412b, according to an aspect of the present disclosure. In particular the skin graft 24 is sutured to the circumferential skin edge 26 and into the bed 412b by a plurality of sutures 30. In addition, several of the sutures 30 are left long (hereafter referred to as "long sutures 430") and extend radially outward from the circumferential skin edge 26 as illustrated in FIG. 4G. The length of each long suture 430 is equal to or greater than at least two times a diameter of the skin graft 24, and may be extend past the outer diameter of the breast mound of the breast 10.

Figure 4H:
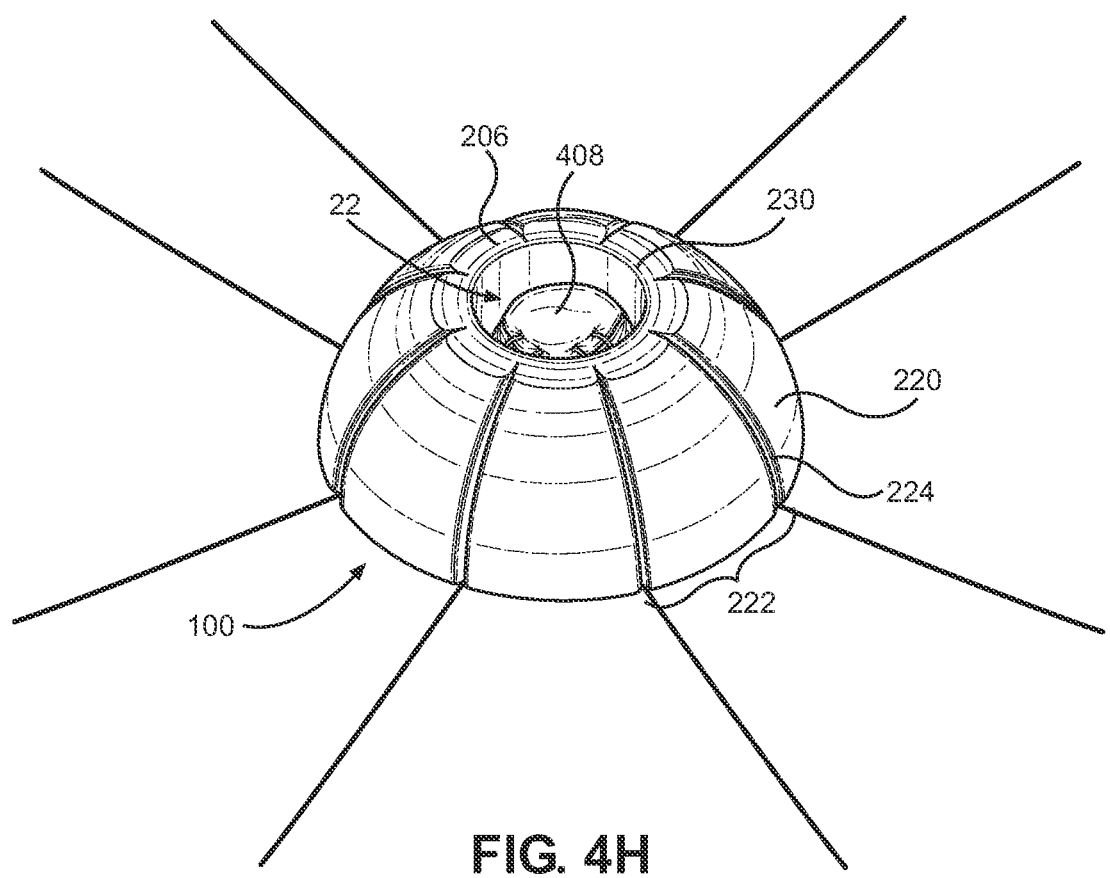
FIG. 4H illustrates a process of positioning a cover device on a NAC, according to an aspect of the present disclosure.

FIG. 4H illustrates a process of positioning the cover device 100 on the NAC 20, according to an aspect of the present disclosure. As illustrated in FIG. 4H, a cover device, for example the cover device 100 illustrated in FIGS. 1-2D, is positioned on the skin graft 24 of the NAC 20, and the nipple 22 of the NAC 20 is inserted into the channel 210. Prior to positioning the cover device 100 on the NAC 20, the cover device 100, which may have been gamma sterilized, is removed from a sterilized packaging. The tip of the nipple 22 is defined by the cap 408, which is sutured to the wings 408 of the flap 404. A location of the cap 408 along an axis of the channel 210 is between the first end face 206 and the second end face 208. More specifically, a height of the nipple 22 may be less than the height A of the cover device 100. Accordingly, the cover device 100 will protrude from the breast 100 past the tip of the nipple 22 and is thus configured to enclose and protect the nipple 22 from external forces (e.g. pressure/rubbing from garments).

As further illustrated in FIG. 4H, each groove 224 is aligned with a respective long suture 430 extending from the outer diameter of the skin graft 24/circumferential skin edge 26 of the breast 10. A number of long sutures 430 may be equal to a number of the grooves 224. According to an aspect of the present disclosure, there is one long suture 430 for each one of eight grooves 224. However, the cover device 100 may be secured to the NAC as discussed in more detail with reference to FIG. 4I, by more or less grooves 224 and corresponding long sutures 430. For example, the cover device 100 may be provided with three, four, or six grooves 224 and a corresponding number of long sutures 430 may be provided during the suturing process illustrated in FIG. 4G.

According to another aspect of the present disclosure, the number of long sutures 430 may not have to be equal to the number of grooves 224. The number of grooves 224 and sutures 430 must be such that a provided number of potential grooved suture combinations 440, which are illustrated in FIG. 4I and discussed below, is suitable to secure the cover device 100 to the NAC 20 with the second end face 208 pressed against a surface of the skin graft 24 as discussed below with reference to FIGS. 5 and 6.

Figure 4I:
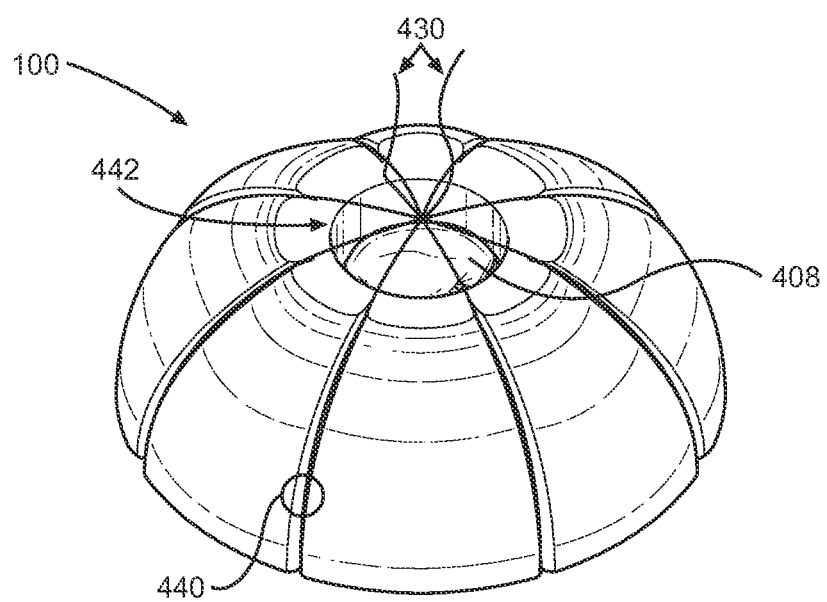
FIG. 4I illustrates a process of securing a cover device to a NAC, according to an aspect of the present disclosure.

FIG. 4I illustrates a process of securing the cover device 100 to the NAC 20, according to an aspect of the present disclosure. FIG. 4I illustrates a plurality of the grooved suture combinations 440 in which a respective long suture 430 has been positioned within a corresponding second groove end 228, groove 224, first groove end 226, and notch 230. Accordingly, the long sutures 430 are positioned in corresponding grooves 224 between the wall segments 222. Further, the long sutures 430 are tied together inwardly relative to the notches 230 in a tie 442, and thereby apply pressure to the first end face 206. The applied pressure is transmitted through the body 200 to the second end face 208, which applies the pressure to the skin graft 24. Thus, the cover device 100 applies pressure to the skin graft 24 of the NAC 20. At the same time, the head 202, first end face 206, and inner surface 212, together with the tie 442 and portions of the long sutures 430 extending radially between the tie 442 and the first end face 206, protect the nipple 22 of the NAC 20.

Figure 5:
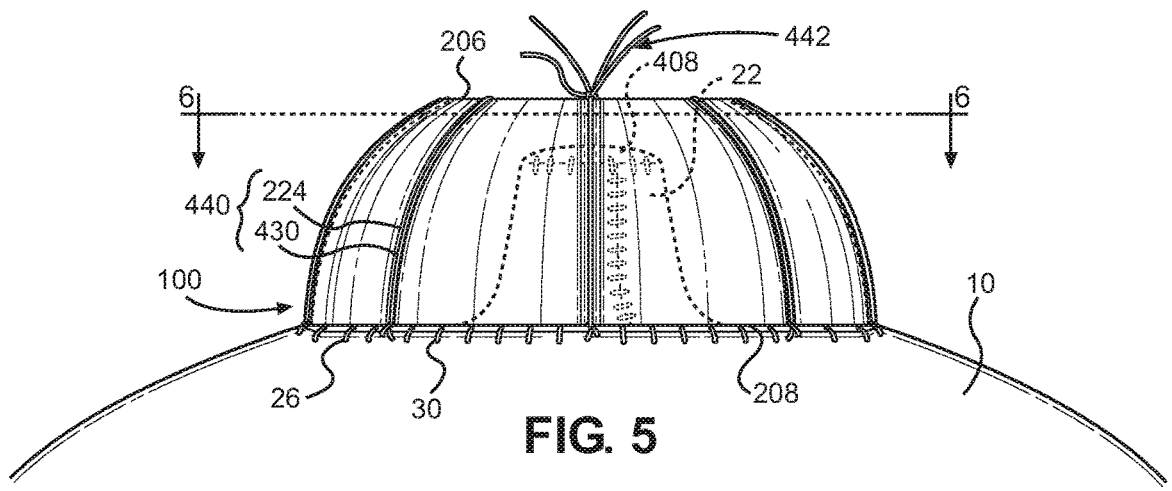
FIG. 5 illustrates a side elevation of a breast with a cover device secured to the breast, according to an aspect of the present disclosure.

FIG. 5 illustrates a side elevation of the breast 10 with a cover device 100 secured to the breast 10, according to an aspect of the present disclosure. The nipple 22 is shown within the cover device 100 by phantom lines. As illustrated in FIG. 5, the long sutures 430 are positioned in the grooves 224 and tied together in the tie 442. The second outer diameter C of the cover device 100 (i.e. of the second end face 208) may substantially correspond the circumferential skin edge 26/outer diameter of the skin graft 24. According to an aspect of the present disclosure, the second outer diameter C may be slightly less than the diameter of the circumferential skin edge 26, and as a result, the long sutures 430 may have to be moved/pulled radially inward relative to the circumferential skin edge 26/outer diameter of the skin graft 24, to be positioned within the second groove ends 228 and run through the grooves 224. According to another aspect of the present disclosure, the second outer diameter C may be slightly more than the diameter of the circumferential skin edge, such that portions of the long sutures 430 extending immediately from the circumferential skin edge 26/outer diameter of the skin graft 24 will be positioned (e.g. tucked) between the cover device 100 and the skin immediately surrounding the circumferential skin edge 26.

Figure 6:
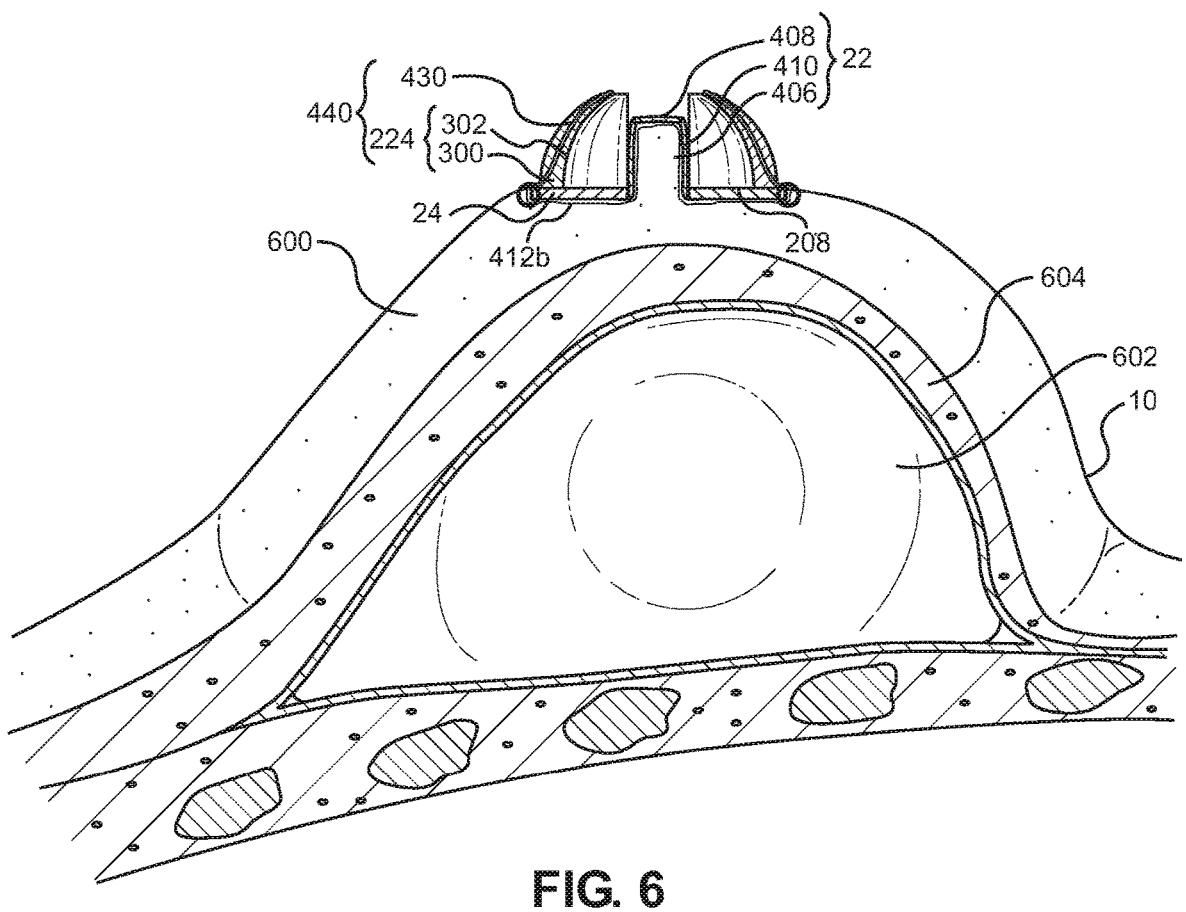
FIG. 6 illustrates a cross-sectional view of a breast taken along section line 6-6 of FIG. 5.

FIG. 6 illustrates a cross-sectional view of the breast 100 along section line 6-6 of FIG. 5. In particular, FIG. 6 illustrates the location of the skin graft 24 relative to fatty tissue 600 of the breast 10. As part of a breast reconstruction that may be performed in tandem with or separately from a mastectomy, an implant 602 may be inserted into the breast 10 through an incision (not shown) and may be partially covered by a pectoral muscle 604. Thus, the pectoral muscle 604 will be located within the breast 10 between the implant 602 and the fatty tissue 600. However, one of ordinary skill in the art will recognize that the implant 602 may not always be placed under the pectoral muscle 604. In particular, the implant 602 may be laid directly on top of the pectoral muscle 604 directly under the fatty tissue 600 of the skin of the breast 10 once the breast tissue has been removed. Subsequent to the procedure in which the implant 602 is inserted into the breast 10, the NAC 20 may be reconstructed at the apex of the breast 10 in a procedure as discussed above with reference to FIGS. 4A-4I. The cover device 100 of the present disclosure aids in the construction of both an areola and a nipple of a NAC as discussed in more detail below.

It is well known in the art to utilize skin grafts to form areolas in NAC reconstruction procedures as illustrated in FIGS. 4E-4F. A skin graft of a reconstructed NAC must be vascularized by blood vessels in the dermis of a de-epithelialized bed created in/on the breast. Successful revascularization will result in the blood vessels growing into the dermis of both a full or split-thickness skin graft and thereby attaching the skin graft to the de-epithelialized bed. This may be referred to as the skin graft "taking" to the de-epithelialized bed in which the skin graft is sustained by, and becomes a part of, the tissue and skin surrounding the location where the skin graft is applied.

In contrast, if the skin graft is not revascularized by the blood vessels in the de-epithelialized bed, the skin graft will die and be unusable. One cause of the skin graft not "taking" may be from blood accumulation in one or more small areas (e.g. pockets, divots, etc.) between the de-epithelialized bed and the skin graft. This can occur if a pressure pushing the skin graft onto the de-epithelialized bed is not evenly applied over the surface area of the skin graft.

It is well known in the art to employ split-thickness skin grafts or full-thickness skin grafts for NAC reconstruction procedures. A split-thickness skin graft is typically a raw surface with a portion of a dermis thereof removed. Split-thickness skin grafts may be taken from a donor site in slices with a device such as dermatome, and are often used for burns. A split-thickness skin graft, as compared to a full-thickness graft, may heal more rapidly. However, the donor site for a split thickness skin graft leaves a raw surface that has to heal by migration of skin cells from the residual skin appendages (sweat glands, hair follicles) remaining in a lower level of the dermis left behind by the taking of only an upper portion of the dermis (hence "split thickness") with the skin graft.

A full-thickness skin graft is often taken from a part of the body with loose skin, and the donor site for the full-thickness skin graft is sutured together once the graft is removed. All fat underneath the skin graft is removed but a full-thickness of a respective dermis and epidermis remain. Revascularization of a full-thickness skin graft may be more difficult/take longer than a split-thickness skin graft generally. Thus, a potential for loss of a full-thickness skin graft (i.e. dying and having to be replaced), may be greater than for a split-thickness skin graft. However, as is typically the case, once an areola of a NAC has been reconstructed from a skin graft (either split or full-thickness), the resulting reconstructed areola may have to be colorized through a tattooing procedure to give the appearance of a normal/natural NAC. A reconstructed areola formed from a full-thickness skin graft may be thicker and more suitable (e.g., more sturdy, less sensitive, etc.) for such a tattooing procedure than a split-thickness skin graft.

Aspects of the cover device 100 of the present disclosure include a flat surface of the second end face 208 that applies pressure evenly to the skin graft 24 upon the log sutures 430 being tied. As a result, the cover device 100 of the present disclosure may facilitate improved revascularization of either of a spilt- or full-thickness skin graft, relative to a method employing a bolster or syringe barrel, or other methods known in the art.

As illustrated in FIG. 6, the skin graft 24 is located between the bed 412b and the second end face 208 of the cover device 100. The bed 412b is a raw surface of the fatty tissue 600 from which the epidermis has been removed, and to which the skin graft 24 must successfully attach. Two long sutures 430 are also illustrated within respective grooves 224. When the long sutures 430 are tied together, in the tie 442, the cover device 100 presses the skin graft 24 towards the fatty tissue 600. As previously explained, the application of pressure is facilitated in part by the configuration of the grooves 224, the first groove ends 226, and notches 230 that provide the transitions from the outer surface 220 to the first end face 206. Said transitions promote uniform transmission and application of downward forces onto the first end face 206, which are evenly transmitted by the second end face 208 to the skin graft 24. Further, due to the flat, continuous, and even surface of the second end face 208; the second end face 208 applies pressure substantially evenly to the surface of the skin graft 24. As a result of the cover device 100 pressing the skin graft 24 towards the fatty tissue 600, the cover device 100 pushes out fluid between the skin graft 24 and the bed 412b, and facilitates vascularization by the blood vessels in the bed 412b of the skin graft 24. In addition, the cover device 100 may help prevent the skin graft 24 from becoming ulcerated.

As discussed above, it is imperative that a skin graft (split or full) of a reconstructed NAC be pressed evenly over a respective surface area on to a receiving bed. The cover device 100 accomplishes this via the flat second end face 208 being pressed down by the tied long sutures 430 which secure the cover device 100 to the NAC 20 as illustrated in FIGS. 4I, 5, and 6. In addition, as a result of the properties of the material from which the cover device 100 is composed, the body 200 of the cover device 100 constitutes an elastic solid structure that maintains a respective shape if a force applied thereto remains static. Accordingly, the cover device 100 is more easily and reliably maintained in its respective form, as applied immediately after nipple reconstruction, as well as a subsequent variable amount of time, as compared to other methods such as the use of a bolster. Therefore, the attendant advantages of using a full-thickness skin graft may be obtained more reliably as compared to a bolster, for example, because the cover device 100 of the present disclosure can be utilized more easily to apply a uniform and constant pressure for a time required for a full-thickness skin graft of a reconstructed NAC to take (become vascularized and attach to a bed).

Employing a skin graft (full or split) may provide advantages as compared to known NAC reconstruction methods in which a skin graft is not utilized. Unlike methods in which a skin graft is used, scars from reconstructing a nipple may remain visible through tattooed pigment for methods in which a skin graft is not utilized. This may occur as pigment uptake is not uniform in said scars. Hence the technique of providing a smooth uniform surface (healed skin graft) in order to obtain a non scar bearing surface for uniform and more cosmetically acceptable uptake of tattoo pigment is often preferred. However, the cover device 100 of the present disclosure may be used and provide advantages in NAC reconstructions where a skin graft is not used.

Other methods for NAC reconstruction may not implement the use of a skin graft to form an areola. However, as part of a majority, if not all NAC reconstructions, nipple reconstruction procedures commonly involve cutting a flap to wrap around a central core of fatty tissue, which then acts as a blood supply and ultimately as a "fill" within a healed nipple. As illustrated in FIGS. 4I, 5, and 6, the cover device 100 of the present disclosure facilitates the construction of the nipple 22 of the NAC 20 as a result of the inner surface 212 of the body 200 that defines the channel 210, which receives the nipple 22. The inner surface 212 helps mold the nipple 22 by preventing it from slumping, while at the same time protects the nipple 22 since the channel 210 is longer than the nipple 22 and thereby prevents a top of the nipple 22 from being exposed. Accordingly, the cover device 100 of the present disclosure can be effectively used to construct and protect a NAC whether a skin graft is used for the areola reconstruction or not.

Figure 7B:
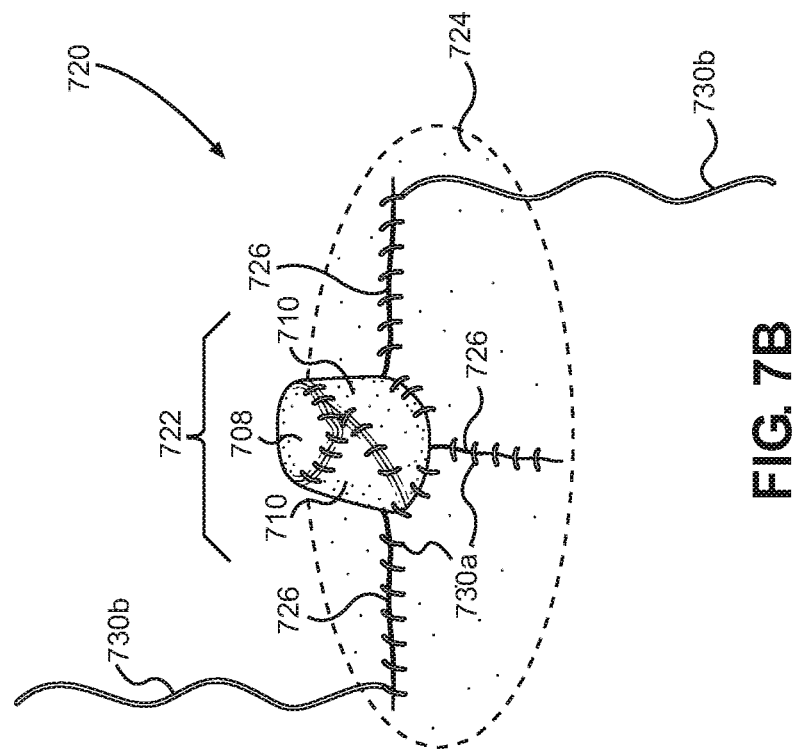
FIG. 7B illustrates front perspective view of a reconstructed NAC, according to an aspect of the present disclosure.
Figure 7A:
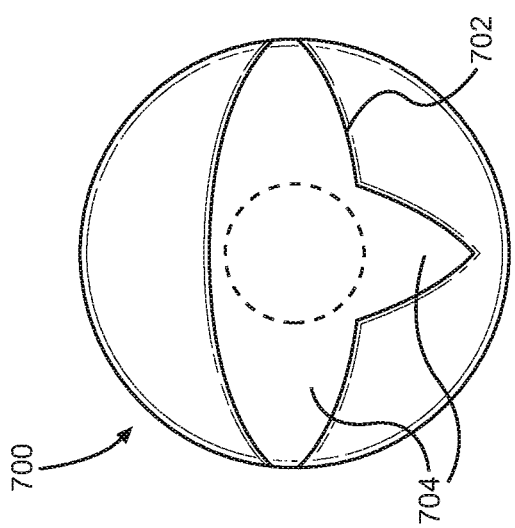
FIG. 7A illustrates an overhead view of a proposed position for a NAC, according to an aspect of the present disclosure.

FIG. 7A illustrates an overhead view of a proposed position 700 for a NAC 720 for a procedure in which a skin graft is not utilized. FIG. 7A further illustrates a flap outline 702 that once incised along, will provide a skate flap and correspond to a donor site 704 on a breast mound. This type of NAC reconstruction (i.e. flap type reconstruction) may be employed where skin of a breast construction is lax enough to be pulled together without distorting a shape of the breast mound. It will be understood that other flap types (e.g. star, S-flap, etc.) may be used for this type of NAC reconstruction in which only a nipple is surgically reconstructed and an areola may be created through tattooing alone.

FIG. 7B illustrates a front perspective view of the NAC 720 after a nipple 722 has been reconstructed from a cap 708 and wings 710 that defined the skate flap provided by incision along the flap outline 702 illustrated in FIG. 7A. Typical of this type of NAC reconstruction, in the absence of placing a skin graft for an areola, the donor site 704 left by the elevation of skin/fat of the cap 708 and wings 710 is closed by suturing opposing skin edges 726 together with sutures 730*a*. Skin 724 of the breast mound around the nipple 722 will need to be tattooed in order to produce a facsimile of a different colored areola from surrounding breast skin. The tattoo pigment will need to be placed in to scars from the sutured incisions used to close the donor site 704 left by the elevation of the cap 708 and wings 710.

As illustrated in FIG. 7B, the NAC 720 is provided with long sutures for securing the cover device 100 to the skin 724, which is designated in FIG. 7B by a dotted line 725 surrounding the nipple 722. The flat surface of the second end face 208 applies pressure evenly to the skin edges 726 sutured together. Accordingly, attachment and healing of each pair of the skin edges 726 extending from the nipple 722 occurs under the same uniform conditions over a complete length respectively thereof as facilitated by the cover device 100 of the present disclosure.

Figure 8:
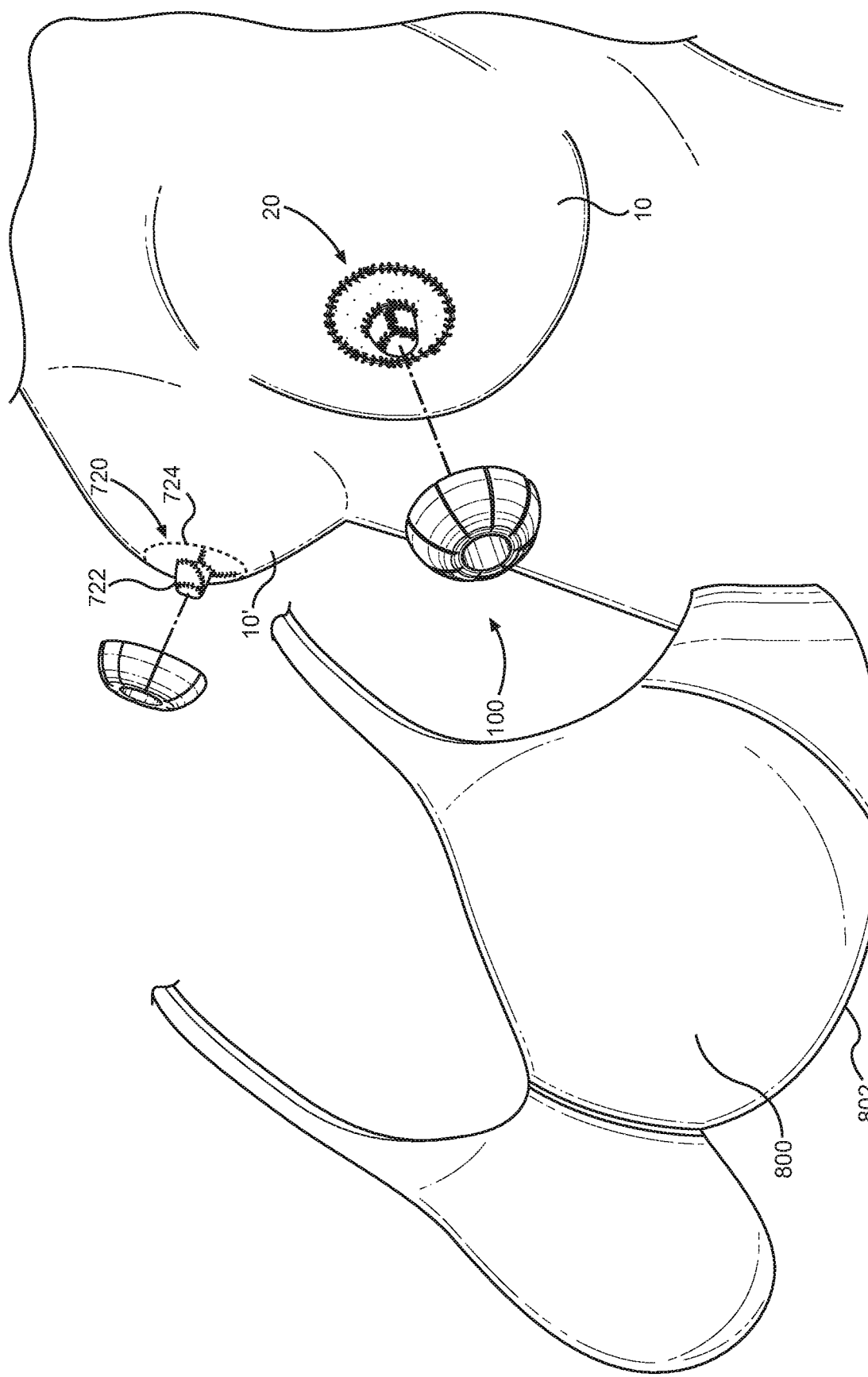
FIG. 8 illustrates a state of a pair of breasts prior to being positioned in a breast support device with a cover device, according to an aspect of the present disclosure.

FIG. 8 illustrates a state of a pair of breasts 10, 10' prior to being positioned in a breast support device 800 with cover devices 100, according to an aspect of the present disclosure. As can be seen, the breast 10 in the forefront of FIG. 8 includes the NAC 20 illustrated in FIGS. 4G-6, and the breast 10' in the foreground of FIG. 8 includes the NAC 720 illustrated in FIG. 7B. One of ordinary skill in the art will recognize that the same NAC reconstruction procedure may be performed for both breasts of a patient as illustrated in FIG. 1, or different NAC reconstructions may be performed as illustrated in FIG. 8. FIG. 8 includes both NAC types in order to demonstrate the applicability of the cover device 100 to different NAC reconstruction procedures.

The long sutures 430, 730*b* and the cover device 100 may be removed 7 to 10 days after the NAC reconstruction procedure (nipple reconstruction in the case of the NAC 720) so that each NAC 20, 720 may be examined and evaluated from a healing (which in the case of NAC 20 would include taking of the skin graft 24) standpoint. FIG. 8 illustrates the state of each breast 10, 10' after the long sutures 430 and cover device 100 have been removed and prior to the remaining sutures 30 being removed which would normally occur during such an examination. Once all the sutures 30 have been removed from each NAC 20, 720 the cover device 100 may continue to be used to protect each NAC 20, 720 without being fixedly secured to thereto, respectively.

During an examination of the type mentioned above, the same cover device 100 that was secured to each of the breasts 10, 10' may be removed, cleaned, and again positioned on a respective NAC 20, 720 to be held in place by a cup 802 of the breast support device 800. However, it will be understood that the cover device 100 is made of a material (e.g. ethyl vinyl acetate or the like) such that the cover device 100 is easily replaceable if desired. Thus, the same or a new cover device 100 may be utilized as a protective device to prevent injury to the newly constructed NAC 20,720, especially the nipple 22,722 in the ensuing weeks until the NAC 20,720 is deemed sufficiently healed to withstand normal "wear and tear" trauma from clothing and/or physical activity.

Figure 9:
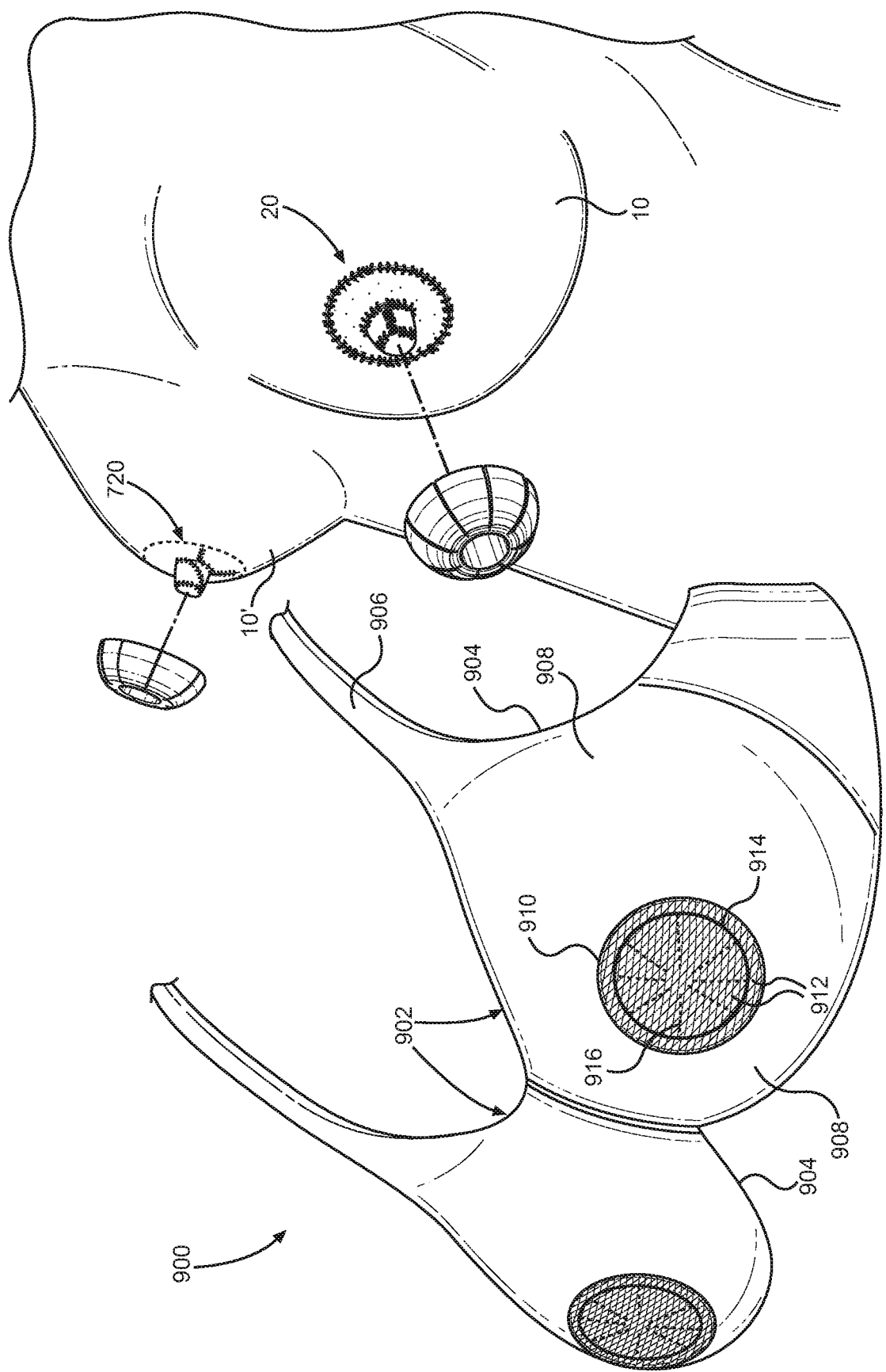
FIG. 9 illustrates a state of a pair of breasts prior to being positioned in a breast support device with a cover device, according to an aspect of the present disclosure.

FIG. 9 illustrates a state of the pair of breasts 10, 10' prior to being positioned in a breast support device 900 with cover devices 100, according to an aspect of the present disclosure. The breast support device 900 includes a cup 902 configured to support each breast 10, and each cup 902 may include a padded region 908 extending immediately from an outer edge 904 and straps 906 of the breast support device 900. The padded region 908 may surround an intermediate edge 910 that surrounds and attaches an elastic region 912 to the padded region 908. The elastic region 912 may be made of a stretchable and breathable elastic fabric (e.g. polyester), and may be more flexible than the padded region 908.

A diameter of the elastic region 912 may be 1.0 to 2.0 cm larger than a diameter of a typical NAC 20,720 that has been reconstructed. Further, the elastic region 912 may include a seam 914 that is concentric with the intermediate edge 910 and has a diameter that is slightly greater than the typical reconstructed NAC 20,720. A plurality of strips 916 may extend from the seam 914 towards the center of the elastic region 912 and have a length and cross-section corresponding to the length and cross-section of the grooves 224 of the cover device 100. The strips 916 will function to help secure the cover device 100 in place once the long sutures 430,730b are removed such that the nipple 22,722 of the NAC 20,720 is not solely responsible from holding the cover device 100 in place surrounding the nipple 22,722. Therefore, the breast support device 900 illustrated in FIG. 9 is constructed to hold the cover device 100 in place once the long sutures 430,730b have been removed.

Figure 10:
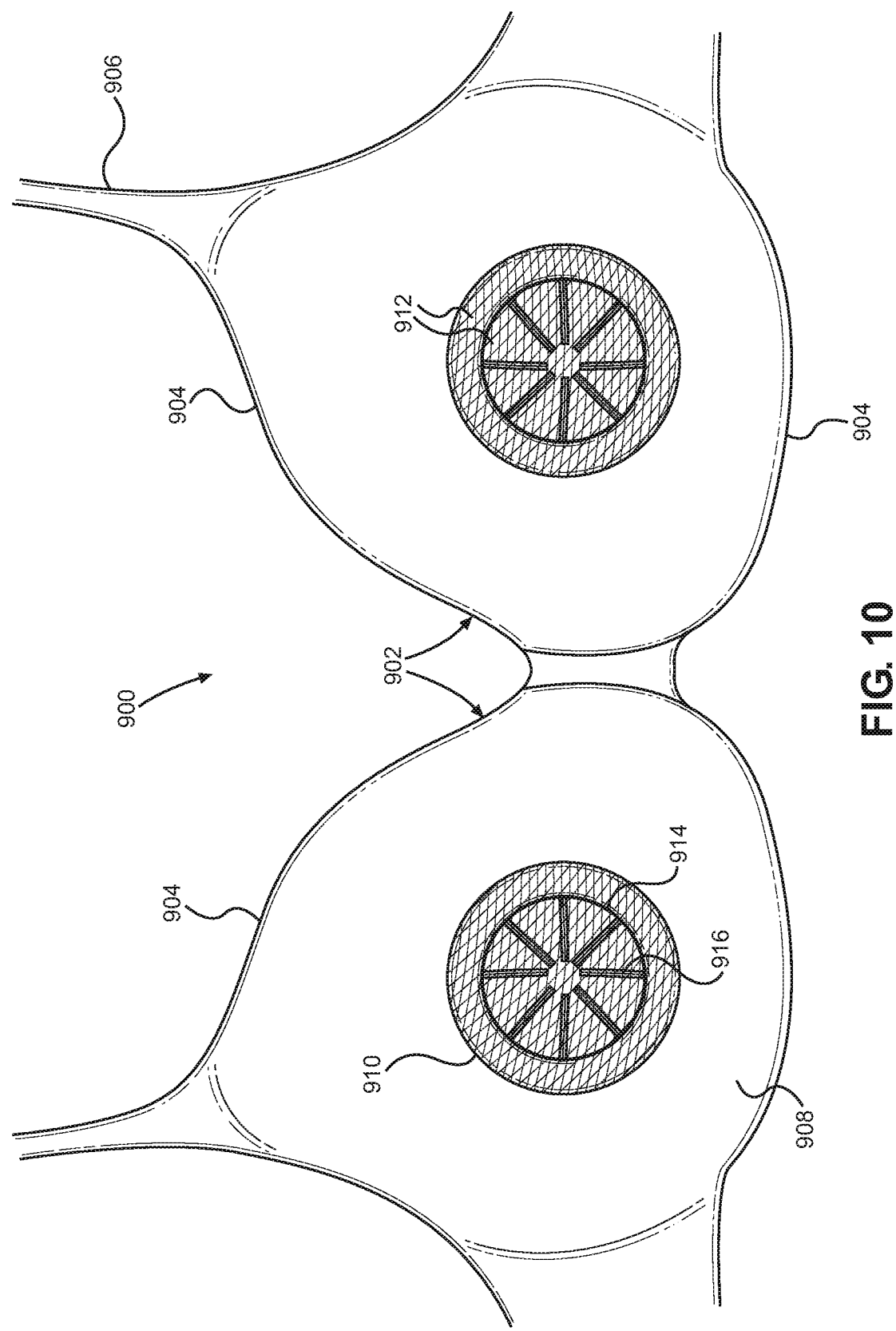
FIG. 10 illustrates an elevation view of an inner cup surface of a breast support device, according to an aspect of the present disclosure.

FIG. 10 illustrates an elevation view of an inner cup surface of the breast support device 900, according to an aspect of the present disclosure. As illustrated in FIG. 10, the strips 916 extend from an inner surface of the elastic region 912. Thus, the cover device 100 can be fitted on to the strips 916 and together with the breast support device 900 can be positioned and secured on a patient with the straps 906 of the breast support device 900. Alternatively, the cover device 100 can be positioned on the breast 10 (or breasts), and the breast support device 900 can be positioned on the cover device(s) 100. According to an aspect of the present disclosure, the strips 916 may extend from the inner cup surface of the breast support device 900 and fit into the grooves 224 such that the outer surface 220 of the cover device 100 is flush with the inner surface of the elastic region 912. According to another aspect of the present disclosure, the strips 916 may be sized to fit into the grooves 224 such that a gap is provided between the outer surface 220 of the cover device 100 is flush with the inner surface of the elastic region 912.

It will be appreciated that the foregoing description provides examples of the disclosed cover device and techniques for applying the cover device. These examples given above are merely illustrative and are not meant to be an exhaustive list of all possible designs, aspects, applications or modifications of the disclosure. Further, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

We claim:

1. A cover device comprising:
    a body including an inner surface and an outer surface, each of the inner surface and the outer surface extending from a first end face of the body to a second end face of the body,
    wherein the inner surface defines a channel extending through the body from the first end face to the second end face,
    wherein the outer surface defines a plurality of grooves extending from the first end face to the second end face, portions of each groove of the plurality of grooves being defined by the first end face and the second end face,
    wherein each of the body, the inner surface, and the outer surface are configured to elastically deform relative to at least an axis of the channel,
    wherein the second end face defines a substantially flat surface configured to evenly distribute an external force applied to at least one of the outer surface and the first end face, and
    wherein the second end face surrounds the channel, and the channel is configured to receive and surround a nipple of a nipple/areola complex of a breast.

2. The cover device of claim 1, wherein an outer diameter of the first end face is less than an outer diameter of the second end face.

3. The cover device of claim 1, wherein the outer surface defines a plurality of wall segments between adjacent grooves of the plurality of grooves.

4. The cover device of claim 3, wherein each wall segment defines a surface that is curved outwardly from an outer circumference of the first end face to an outer circumference of the second end face.

5. The cover device of claim 1, wherein the body is formed from ethyl vinyl acetate.

6. The cover device of claim 1,
    wherein each of the plurality of grooves extends from a first groove end formed in the first end face to a second groove end formed in the second end face, and
    wherein each first groove end extends from a perimeter of the first end face and terminates in a form of a notch in the first end face.

7. The cover device of claim 6,
    wherein a curved slope of each of the plurality of grooves and a respective first groove ends combined with a respective notch defines a continuous transition from the respective first groove end to a flat surface of the first end face.

8. The cover device of claim 1,
    wherein each of the plurality of grooves extends from a groove end formed in the second end face and is defined by a pair of groove walls, and
    wherein each pair of groove walls is symmetric about a joint edge that is located at a center of a trench defined by a respective one of the plurality of grooves.

9. A method of constructing and protecting a nipple/areola complex of a breast, the method comprising:
    suturing a skin graft corresponding to an areola of the nipple/areola complex in a de-epithelialized bed surrounding a nipple of the nipple/areola complex;
    leaving a plurality of long sutures during the suturing, each of the plurality of long sutures extending over a length from an outer circumference of the skin graft that is equal to at least twice the diameter of the skin graft;
    positioning a cover device relative to the nipple/areola complex such that:
        the nipple is positioned within a channel defined by an inner surface of a body of the cover device with a cap of the nipple positioned between a first end face and a second end face of the body of cover device, and
        the second end face abuts a surface of the skin graft;

positioning each of the plurality of long sutures in a respective groove defined by an outer surface of the body of the cover device; and tying the plurality of long sutures together at the first end face and applying an external force to at least one of the outer surface and the first end face such that the cover device is secured to the nipple/areola complex with the second end face in fixed abutment with the surface of the skin graft, wherein the inner surface defines the channel as extending through the body from the first end face to the second end face, wherein the outer surface defines the plurality of grooves as extending from the first end face to the second end face, portions of each groove of the plurality of grooves being defined by the first end face and the second end face, wherein each of the body, the inner surface, and the outer surface are configured to elastically deform relative to at least an axis of the channel, wherein the second end face defines a substantially flat surface configured to evenly distribute the external force applied to the at least one of the outer surface and the first end face by the plurality of sutures, and wherein the second end face surrounds the channel, and the channel receives and surrounds the nipple.

10. The method of constructing and protecting the nipple/areola complex of claim 9, wherein the body is formed from ethyl vinyl acetate.

11. The method of constructing and protecting the nipple/areola complex of claim 9, wherein each groove defined by the outer surface of the cover device extends from a first groove end formed in the first end face to a second groove end formed in the second end face, and wherein each first groove end extends from a perimeter of the first end face and terminates in a form of a notch in the first end face.

12. The method of constructing and protecting the nipple/areola complex of claim 11, wherein a curved slope of each groove defined by the outer surface of the cover device and a respective first groove end combines with a respective notch to define a continuous transition from the respective first groove end to a flat surface of the first end face, and wherein tying the plurality of long sutures includes each suture following a path of a respective transition such that a downward force is applied to the first end face by each suture.

13. The method of constructing and protecting the nipple/areola complex of claim 9, further comprising:

removing the long sutures and the cover device from the nipple/areola complex;

cleaning the cover device;

positioning the cover device on the nipple/areola complex; and positioning a breast support device on the breast, wherein the cover device is configured to be secured to the nipple/areola complex by the breast support device.

* * * * *